United States Patent [19]

Pieri et al.

[11] 4,268,436
[45] May 19, 1981

[54] PROCESS FOR PREPARING DIAZONIUM SALTS OF 3-AMINO-PYRAZOLE

[75] Inventors: Giampiero Pieri, Saronno; Enzo Rosati, Seregno; Ruggero Battisti, Novara; Giovanni Burei, Seregno, all of Italy

[73] Assignee: Aziende Colori Nazionali Affini Acna S.p.A., Milan, Italy

[21] Appl. No.: 41,550

[22] Filed: May 23, 1979

[30] Foreign Application Priority Data

May 24, 1978 [IT] Italy .............................. 23725 A/78

[51] Int. Cl.³ ................. C07C 107/00; C07C 107/04; C07C 107/08; C07C 113/04
[52] U.S. Cl. ................................... 260/141; 260/156; 260/162; 260/163; 546/135; 548/162; 548/375; 548/377
[58] Field of Search ................... 260/141 P, 141 H; 548/373

[56] References Cited

U.S. PATENT DOCUMENTS

| | | | |
|---|---|---|---|
| 2,432,034 | 12/1947 | Nies | 260/141 X |
| 3,597,412 | 8/1971 | Mohr et al. | 260/146 T |
| 3,793,305 | 2/1974 | Balon | 260/154 |
| 3,822,247 | 7/1974 | Ozutsumi et al. | 260/157 |
| 4,149,005 | 4/1979 | Battisti et al. | 548/362 |

FOREIGN PATENT DOCUMENTS 977326   12/1964   United Kingdom ................ 260/141

OTHER PUBLICATIONS

Iwanoff, Ber. Deut. Chem. Gesell., vol. 87, pp. 1600–1604 (1954).
Reimlinger et al., Ber. Deut. Chem. Gesell., vol. 94, pp. 1036–1041 (1961).
Houben–Weyl, "Methoden der Organischen Chemie", vol. X/3, pp. 58–66 (1965).

Primary Examiner—Floyd D. Higel

[57] ABSTRACT

3-Diazonium salts of pyrazole, useful as intermediates in the preparation of azo dyes are obtained by an oxidative diazotization of 3-amino-pyrazolines with nitrous acid or with nitrosyl-sulphuric acid. The 3-diazonium salts of pyrazole have the following structure:

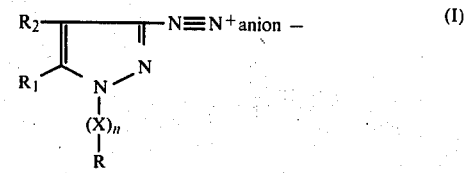

wherein:
X is a radical —CO— or —COO—,
n is 0 or 1,
R is hydrogen (in such case n is always 0), a normal or ramified alkyl $C_1$—$C_4$, an aromatic or heterocyclic, optionally substituted, radical, in particular a phenyl radical having the structure:

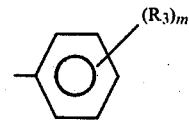

in which
m may vary from 0 to 3 and substituents $R_3$, either like or unlike one another for m>1, are alkyls $C_1$—$C_4$ with linear or ramified chain, halogens, a cyano, nitro, sulphonic or carboxylic group, carboxyesters having a linear or ramified chain $C_1$—$C_4$, alkoxyls having a linear or ramified chain $C_1$—$C_4$, trifluoromethyl groups, acylamino groups having a linear or ramified aliphatic chain $C_1$—$C_4$, or sulphonamide groups of the type

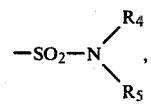

wherein substituents $R_4$ and $R_5$, like or unlike each other, are hydrogen, or linear or ramified aliphatic chains $C_1$—$C_4$, and
$R_1$ and $R_2$, either like or unlike each other, are hydrogen, linear or ramified aliphatic chains $C_1$—$C_4$, or non-substituted or substituted benzene residues.

5 Claims, No Drawings

PROCESS FOR PREPARING DIAZONIUM SALTS OF 3-AMINO-PYRAZOLE

THE PRIOR ART

It is known that the diazonium salts in position 3 of pyrazole and, in particular, the derivatives of structure (I), can be obtained by diazotizing suitable 3-amino-pyrazoles with nitrous acid, or with nitrosyl-sulphuric acid, operating according to conventional modalities in the presence of strong mineral acids, such as hydrochloric acid, sulphuric acid or phosphoric acid.

Some examples of such diazotizations are described in the U.S. application of Ruggero Battisti et al. Ser. No. 809,848, filed June 24, 1977, now U.S. Pat. No. 4,216,145, issued Aug. 5, 1980) in which some monoazo dyes useful for dyeing and printing hydrophobic synthetic fibers are disclosed.

According to the prior art, the preparation of 3-amino-pyrazoles, intermediates of the diazonium salts of structure I, is rather arduous.

Thus, one of the prior art processes involves condensation of the suitable hydrazino-derivatives with $\alpha$-$\beta$ unsaturated nitriles in the presence of organic bases (e.g., choline hydrate), followed by a short boiling with a mineral acid (Il Farmaco-Ed. Sc. vol. XIX, 7, page 638), to obtain, for example, some 3-amino-pyrazolines of structure II:

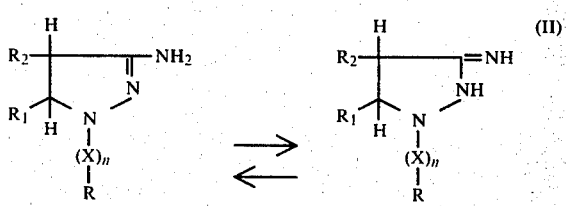

wherein X, n, R, $R_1$, $R_2$ have the same meanings as in structure (I).

Another known method for preparing 3-amino-pyrazolines of structure (II) consists in condensing the hydrazino-derivatives with the $\alpha$-$\beta$ structure nitriles in an alcohol solution in the presence of alkaline alkoxides (Ilford Ltd. British Pat. No. 679,678).

The 3-amino-pyrazolines of structure (II) can be dehydrogenated to give the corresponding 3-amino-pyrazoles of structure (III):

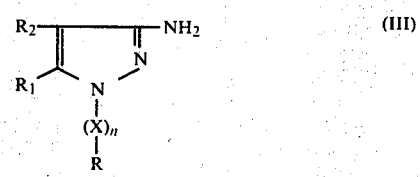

[wherein X, n, R, $R_1$, $R_2$ have the meanings as in structure (I)] according to various conventional methods. Dehydrogenations carried out with sulphur, ferric sulphate, bromine, bromosuccinimide, yellow mercuric oxide, activated manganese dioxide, lead tetraacetate, tert.butyl chromate, triphenylmethyl perchlorate, as well as catalytic dehydrogenations with carbon-supported palladium, either in the presence or in the absence of hydrogen acceptors, effected both on free amines and on acetyl-derivatives, are described in the chemical literature.

These methods do not give satisfactory results as concerns quality and yield of the products obtained.

The two best processes known to us for preparing 3-amino-pyrazoles (III), precursors of the diazonium salts of structure (I), consist in dehydrogenating a pyrazoline of structure (II) by means of chloranil in xylene (C. Alberti, Il Farmaco, supra), and by making air to pass through an inert solvent in the presence of copper compounds and of organic bases as catalysts (as described in the U.S. application of Ruggero Battisti et al. Ser. No. 809,849 filed June 24, 1977, now U.S. Pat. No. 4,149,005, issued Apr. 10, 1979).

THE PRESENT INVENTION

One object of this invention is to provide a process by which diazonium salts of 3-amino-pyrazole of high quality are obtained in high yield.

This and other objects are accomplished by the present invention in accordance with which diazonium salts of formula (I) are obtained by oxidizing diazotization of 3-amino-pyrazolines of structure (II) with nitrous acid or with nitrosylsulphuric acid.

In practice, the process of this invention is carried out by reacting, at temperatures ranging from $-10°$ C. to $+20°$ C., a solution of 3-amino-pyrazoline (II) in hydrochloric acid, sulphuric acid, phosphoric acid, saturated aliphatic organic acid having an aliphatic chain $C_1$-$C_4$, or mixtures of such acids, with an excess of nitrosylsulphuric acid, of a nitrite of an alkaline metal, or of a nitrite of alkyl or isoalkyl.

The molar ratio between the nitrous acid or nitrosylsulphuric acid and 3-amino-pyrazoline (II) may vary from 2 to 5.

The 3-amino pyrazolines of structure (II) which are useful for obtaining the diazonium salts of structure (I), and which we have used for that purpose include:

3-amino-1-N-acetyl-pyrazoline,
3-amino-1-N-propionyl-pyrazoline,
3-amino-1-N-benzoyl-pyrazoline, 3-amino-1-N-(4'-chloro-benzoyl)-pyrazoline,
3-aminoo-1-N-carboxyethylester-pyrazoline,
3-amino-pyrazoline,
3-amino-1-phenyl-pyrazoline,
3-amino-1,5-diphenyl-pyrazoline,
3-amino-1(3'-tolyl)-pyrazoline,
3-amino-4-methyl-1-phenyl-pyrazoline,
3-amino-5-methyl-1-phenyl-pyrazoline,
3-amino-1(3'-tolyl)-5-phenyl-pyrazoline,
3-amino-1(3'-tolyl)-4-methyl-pyrazoline, 3-amino-1(2'-tolyl)-5-phenyl-pyrazoline,
3-amino-1(4'-methoxyphenyl)-pyrazoline,
3-amino-1-(4'-ethoxyphenyl)-pyrazoline,
3-amino-1-(4'-acetylaminophenyl)-pyrazoline,
3-amino-1-(4'-propionylamino-phenyl)-pyrazoline,
3-amino-1-(2-benzothiazolyl)-pyrazoline,
3-amino-1-(2-quinolinyl)-pyrazoline,
3-amino-1-(2'chlorophenyl)-pyrazoline,
3-amino-1-(3'-chlorophenyl)-pyrazoline,
3-amino-1-(4'-chlorophenyl)-pyrazoline,
3-amino-1-(2'-bromophenyl)-pyrazoline,
3-amino-1-(3'-bromophenyl)-pyrazoline,
3-amino-1-(4'-bromophenyl)-pyrazoline,
3-amino-1-(2',4'-dichlorophenyl)-pyrazoline,
3-amino-1-(2',5'-dichlorophenyl)-pyrazoline,
3-amino-1-(2',6'-dichlorophenyl)-pyrazoline,
3-amino-1-(2',3'-dichlorophenyl)-pyrazoline,
3-amino-1-(3',4'-dichlorophenyl)-pyrazoline,
3-amino-1-(3',5'-dichlorophenyl)-pyrazoline, 3-amino-1-(2',4'-dibromophenyl)-pyrazoline,
3-amino-1-(2',5'-dibromophenyl)-pyrazoline,
3-amino-1-(2',6'-dibromophenyl)-pyrazoline,
3-amino-1-(3',4'-dibromophenyl)-pyrazoline,
3-amino-1-(3',5'-dibromophenyl)-pyrazoline,
3-amino-1-(2',3',4'-trichlorophenyl)-pyrazoline,
3-amino-1-(2',4',5'-trichlorophenyl)-pyrazoline,
3-amino-1-(3',4',5'-trichlorophenyl)-pyrazoline,
3-amino-1-(2',3',4'-tribromophenyl-pyrazoline,
3-amino-1-(2',4',5'-tribromophenyl)-pyrazoline,
3-amino-1-(3',4',5'-tribromophenyl)-pyrazoline,
3-amino-1-(2'-nitrophenyl)-pyrazoline,
3-amino-1-(3'-nitrophenyl)-pyrazoline,
3-amino-1-(4'-nitrophenyl)-pyrazoline,
3-amino-1-(2',4'-dinitrophenyl)-pyrazoline,
3-amino-1-(3',4'-dinitrophenyl)-pyrazoline,
3-amino-1-(2'-cyano-4'-nitrophenyl)-pyrazoline,
3-amino-1-(2'-cyanophenyl)-pyrazoline,
3-amino-1-(3'-cyanophenyl)-pyrazoline,
3-amino-1-(4'-cyanophenyl)-pyrazoline,
3-amino-1-(2'-methoxyphenyl)-pyrazoline,
3-amino-1-(3'-methoxyphenyl)-pyrazoline,
3-amino-1-(4'-methoxyphenyl)-pyrazoline,
3-amino-1-(2'-ethoxyphenyl)-pyrazoline,
3-amino-1-(3'-ethoxyphenyl)-pyrazoline,
3-amino-1-(4'-ethoxyphenyl)-pyrazoline,
3-amino-1-(3',5'-dimethoxyphenyl)-pyrazoline,
3-amino-1-(3',4'-dimethoxyphenyl)-pyrazoline,
3-amino-1-(3'-fluoromethyl-phenyl)-pyrazoline,
3-amino-1-(3'-chlorophenyl)-4-methyl-pyrazoline,
3-amino-1-(3'-chlorophenyl)-5-methyl-pyrazoline,
3-amino-1-(4'-chlorophenyl)-5-phenyl-pyrazoline,
3-amino-1-2'-bromophenyl)-4-methyl-pyrazoline,
3-amino-1-(2'-carboxymethylester-phenyl)-pyrazoline,
3-amino-1-(3'-carboxymethylester-phenyl)-pyrazoline,
3-amino-1-(4'-carboxymethylester-phenyl)-pyrazoline,
3-amino-1-(4'-carboxymethylester-phenyl)-pyrazoline,
3-amino-1-(4'-sulphamido-phenyl)-pyrazoline.

One practical method of carrying out the process of this invention consists in dissolving, at 0°–5° C., the 3-aminopyrazoline of structure (II) in a sufficient amount of an acetic acid/propionic acid mixture in a ratio by weight of 3/1, and in successively adding, at a temperature <10° C., at least 2 moles of 1~2 N nitrosylsulphuric acid for each mole of aminopyrazoline, until the reaction mass, initially violet-blue, turns red and then light brown.

The reaction mass is then placed in water and ice, and the resulting diazo solution is ready for use as coupling agent according to conventional methods well known to those skilled in the art.

An advantageous alternative procedure according to this invention consists in pouring on the excess of nitrosylsulphuric acid, dissolved in acetic acid and/or propionic acid, a sulphuric solution of 3-amino-pyrazoline having structure (II). In this case, neither violet nor red coloring can be noticed, but a light brown mass is obtained at once, which means that the reaction is accomplished.

The aqueous acidic solution of 3-diazo-pyrazole of structure (I) can be analytically characterized—after addition of sulphamic acid in a sufficient amount to remove the excess of nitrous acid—according to various procedures known to those skilled in the art, and which include the following procedures:

(a) The solution is diluted to a prefixed volume in a volumetric flask at a temperature ≦10° C., a portion thereof is withdrawn and decomposed by heating in the presence of copper salts in a $CO_2$ stream, and the nitrogen evolved is collected in an azotometer on 50% potassium hydroxide. 0.1 mole of diazo provides 2240 ml of nitrogen under normal conditions.

(b) The diazo solution is reacted, according to a method known to the technicians skilled in the art, with an alkaline solution buffered by an excess of a strong coupling compound. Preferred coupling compounds are β-naphthol, 1-phenyl-3-methyl-5-pyrazolone, 1,4-dimethyl-3-cyano-6-hydroxy-2-pyridone and similar compounds. The dye obtained is weighed and characterized in a conventional manner and, provided the coupling is the same, is identical with the dye prepared from the 3-amino-pyrazole of structure (III) corresponding to the employed 3-amino-pyrazoline of structure (II).

The following examples are given to illustrate the present invention in more detail and are not intended to be limiting. In the examples, parts stated are by weight unless otherwise specified.

EXAMPLE 1

1.91 parts of 1-(4'-methoxyphenyl)-3-amino pyrazoline having a melting point of 186°–188° C. (0.01 mole), were dissolved under agitation in 60 parts of acetic acid and 20 parts of propionic acid. The solution was cooled down to 0°–5° C., and 20 ml of 1 N solution of nitrosylsulphuric acid in sulphuric acid were gradually poured into it.

The resulting solution of 1-(4'-methoxyphenyl)-3-pyrazole diazonium sulphate was let into 200 parts of ice and 100 parts of water, and the whole was additioned with sufficient sulphamic acid to remove the excess of nitrous acid and then diluted to a volume of 1 liter with iced water.

On the solution, kept at 0° C., the following analyses were carried out:

(a) 100 ml were transferred to a closed 250 ml flask, fed with a $CO_2$ stream and connected, at the outlet, with a 50 ml azotometer filled with a potassium hydroxide aqueous solution at 50% concentration. When all the air was removed by the $CO_2$ stream, the azotometer was set to zero and a solution consisting of 3 parts of rameous chloride in 15 ml of 20 Bé hydrochloric acid was charged through a tap funnel. The flask was gradually heated to a boiling in a bath and was kept under boiling for 15', as long as the volume of nitrogen developed in the meantime in the azotometer remained constant. 21.3 ml of nitrogen, referred to 0° C. and to 760 mm of Hg, was liberated, corresponding to a diazo yield of 95.0% referred to the calculated value.

(b) 10 ml of a 0.1 molar alkaline solution of 1-phenyl-3-methyl-5-pyrazolone, equivalent to 0.001 mole of coupling compound, were diluted with 100 ml of iced water and additioned with 10 g of crystalline sodium acetate. The solution of 1-(4'-methoxyphenyl)-3-pyrazole-diazonium sulphate was gradually added from a burette to the solution containing the crystalline sodium acetate, until a test on filter paper with an aqueous alkaline solution at 2% of hydracid no longer revealed violet shades. To complete the coupling, it was necessary to use 105 ml of the diazo solution, corresponding to a yield of 95.2% referred to the calculated value. The yellow dye so obtained was corresponding to the one prepared by diazotization of 1-(4'-methoxyphenyl)-3-amino-pyrazole obtained according to conventional methods and by coupling on 1-phenol-3-methyl-pyrazolone. On chromatographic analysis on a thin layer of the dye, it was found to be uniform.

EXAMPLE 2

2.19 parts of 1-(4'-carboxyphenyl-methylester)-3-amino pyrazoline, having a melting point of 228–230° C., were dissolved under agitation in 60 parts of acetic acid and 20 parts of propionic acid. The solution was cooled to 0–5° C., and 23 ml of a 1 N solution of nitrosylsulphuric acid in sulphuric acid were gradually poured into it.

The solution of 1-(4'-carboxyphenyl-methylester)-3-pyrazole-diazonium sulphate was let into water and ice, and the excess nitrous acid was removed by the addition of sulphamic acid. After the solution had been diluated to volume with iced water, analyses in analogy with methods(a) and (b) of Example 1 were carried out, with the following results:

according to (a) a diazonium salt yield of 94% referred to the calculated value,
according to (b) a diazonium salt yield of 94.2% referred to the calculated value.

EXAMPLE 3

2.3 parts of 1-)2',4'-dichlorophenyl)-3-aminopyrazoline, having a melting point of 174°–176° C., were dissolved, under agitation, in 60 parts of sulphuric acid, d=1.84, and in 60 parts of acetic acid. Onto this solution cooled to 0°–5° C., 3.26 parts of a 60% aqueous solution of potassium nitrite were gradually poured, maintaining the temperature below 5° C.

The solution of 1-(2',4'-dichlorophenyl)-3-pyrazolediazonium sulphate, after having been let into ice and water, was analyzed according to methods (a) and (b) of Example 1: the diazonium salt yields were respectively of 99.5% and 99.2%, referred to the calculated values.

EXAMPLE 4

1.27 parts of 1-acetyl-3-amino-pyrazoline, having a melting point of 253°–255° C., were dissolved, under agitation, in 50 ml in a 2 N aqueous solution of hydrochloric acid. Onto this solution, cooled down to 0°–5° C., a solution of 1.5 parts of sodium nitrite in 10 ml of water was gradually poured.

The resulting aqueous solution of 1-acetyl-3-pyrazolediazonium sulphate was additioned with a sufficient amount of sulphamic acid to remove the excess nitrous acid. On analyses according to methods (a) and (b) of Example 1, the diazonium salt yields were found to be 93.7% and 93.4%, respectively.

EXAMPLE 5

1.96 parts of 1-(2'-chlorophenyl)-3-amino-pyrazoline, having a melting point of 77°–78° C., were dissolved, under agitation, in 60 parts of sulphuric acid, d=1.84, and 60 parts of acetic acid. Onto this solution cooled to 0°–5° C., 2.9 parts of isoamyl nitrite were gradually poured, keeping the temperature below 5° C. The whole was stirred at 0°–5° C. for 2 hours, whereupon the solution of 1-(2'-chlorophenyl)-3-pyrazolediazonium sulphate was let into water and ice.

After removal of the excess nitrous acid by addition of sulphamic acid, the solution, analyzed according to methods (a) and (b) of Example 1, exhibited diazonium salt yields, respectively, of 95.2% and 94.9%.

Other examples of diazonium salts of structure I prepared and analyzed according to the modalities described in Examples 1 to 5 are recorded in the following table. The indicated yields represent the average of the found values for both analytical methods (a) and (b) of Example 1.

| Ex. No. | 3-amino-pyrazoline utilized | Operating modalities, Ex. No. | % Diazonium salt yield (average between methods (a) and (b) of Ex. 1) |
|---|---|---|---|
| 6 | 1-(4'-nitrophenyl) | 1~2 | 95. |
| 7 | 1-(3'-nitrophenyl) | 1~2 | 94.7 |
| 8 | 1-(3'-4'-dichlorophenyl) | 1~2 | 98.2 |
| 9 | 1-(2',5'-dichlorophenyl) | 1~2 | 96.8 |
| 10 | 1-(4'-chlorophenyl) | 3 | 93.9 |
| 11 | 1-(3'-chlorophenyl) | 3 | 97.5 |
| 12 | 1-(2',4',5'-trichlorophenyl) | 1~2 | 94.1 |
| 13 | 1-(3'-trifluoromethyl-phenyl) | 5 | 95. |
| 14 | 1-(2'-benzothiazolyl) | 1~2 | 30. |
| 15 | 1-(4'-acetyl-aminophenyl) | 5 | 51.4 |
| 16 | 1-(4'-sulphonamido-phenyl) | 5 | 82. |
| 17 | 1-phenyl | 1~2 | 88.2 |
| 18 | 1,5-diphenyl | 1~2 | 40. |
| 19 | 1-phenyl-4-methyl | 1~2 | 45. |
| 20 | 1-(4'-carboxyphenyl) | 1~2 | 84. |
| 21 | 1-(4'-bromophenyl) | 1~2 | 91.6 |
| 22 | 1-(4'-sulphophenyl) | 4 | 85. |

What we claim is:

1. A process for preparing 3-diazopyrazole salts by oxidative diazotization of 3-aminopyrazolines, comprising treating said 3-aminopyrazolines with an oxidizing-diazotization agent selected from the group consisting of nitroxylsulphuric acid, alkaline metal nitrites, alkyl nitrites and isoalkyl nitrites, at a temperature from −10° C. to +20° C. in an acid medium.

2. The process of claim 1, in which diazonium salts in position 3 of pyrazole corresponding to the following structural formula:

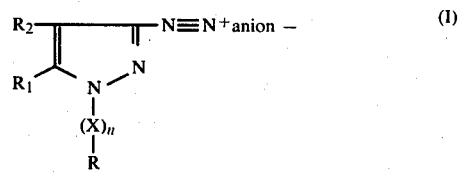

in which
X is a radical —CO or —COO—,
n is 0 or 1,

R is H (in which case n is always 0), a linear or ramified $C_1$—$C_4$ chain, an aromatic or heterocyclic radical, or a substituted aromatic or heterocyclic radical, and $R^1$ and $R^2$, the same or different, are hydrogen, linear or ramified $C_1$—$C_4$ chains, benzene residues, or substituted benzene residues, are prepared by oxidizing diazotization of 3-aminopyrazolines having the structure

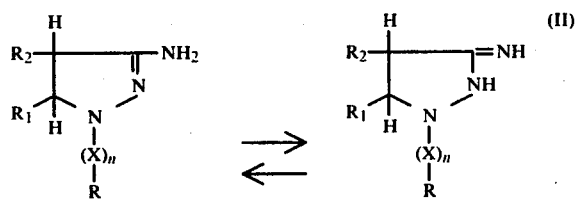

in which X, n, R, $R_1$ and $R_2$ have the same meaning as in structure (I).

3. The process of claim 2, in which in structural formula (I), R is a phenyl radical having the structural formula:

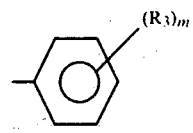

in which m may vary from 0 to 3; and substituents $R_3$, like or unlike each other for m>1, are linear or ramified $C_1$—$C_4$ chains, halogens, cyano, nitro, sulphonic or carboxylic groups, carboxyesters having a linear or ramified $C_1$—$C_4$ chain, alkoxyls having a linear or ramified $C_1$—$C_4$ chain, trifluoromethyl groups, acylamino groups having a linear or ramified $C_1$—$C_4$ chain, or sulphonamido groups of the structure:

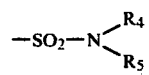

in which substituents $R_4$ and $R_5$, the same or different, are hydrogen or linear or ramified $C_1$—$C_4$ chains.

4. The process of claim 1, in which the oxidizing-diazotization agent and the aminopyrazoline are in a ratio of from 2:1 to 5:1.

5. The process of claim 1, in which the acid medium is selected from the group consisting of mineral acids, saturated aliphatic organic acids and mixtures thereof.

* * * * *